United States Patent
Saar et al.

(10) Patent No.: US 12,122,753 B2
(45) Date of Patent: Oct. 22, 2024

(54) METHOD FOR SOLUBILIZING 5-AMINO-2,3-DIHYDRO-1,4-PHTHALAZINEDIONE

(71) Applicant: MetrioPharm AG, Zürich (CH)

(72) Inventors: Ingo Saar, Niederkassel (DE); Wolfgang Brysch, Berlin (DE); Jörg von Wegerer, Berlin (DE)

(73) Assignee: MetrioPharm AG, Zürich (CH)

( * ) Notice: Subject to any disclaimer, the term of this patent is extended or adjusted under 35 U.S.C. 154(b) by 701 days.

(21) Appl. No.: 16/961,230

(22) PCT Filed: Jan. 10, 2019

(86) PCT No.: PCT/EP2019/000012
§ 371 (c)(1),
(2) Date: Jul. 9, 2020

(87) PCT Pub. No.: WO2019/137825
PCT Pub. Date: Jul. 18, 2019

(65) Prior Publication Data
US 2021/0061771 A1    Mar. 4, 2021

(30) Foreign Application Priority Data

Jan. 11, 2018 (EP) ..................................... 18000019

(51) Int. Cl.
C07D 237/32 (2006.01)
A61K 47/22 (2006.01)
A61K 9/00 (2006.01)

(52) U.S. Cl.
CPC ............ C07D 237/32 (2013.01); A61K 47/22 (2013.01); *A61K 9/0014* (2013.01); *A61K 9/0019* (2013.01); *A61K 9/0053* (2013.01)

(58) Field of Classification Search
CPC .............................. C07D 237/32; A61K 47/22
See application file for complete search history.

(56) References Cited

U.S. PATENT DOCUMENTS

| 2007/0104780 A1 | 5/2007 | Lipari et al. |
| 2010/0222584 A1 * | 9/2010 | Henry .................. C07D 237/32 436/106 |
| 2012/0128610 A1 * | 5/2012 | Nazarova ................. A61K 8/37 424/59 |
| 2012/0202882 A1 | 8/2012 | Banov et al. |

FOREIGN PATENT DOCUMENTS

| CN | 101346128 A | 1/2009 | |
| DE | 19857492 A1 * | 6/2000 | ............... A61K 8/19 |
| EP | 3 290 026 A1 | 3/2018 | |
| WO | WO 03/007907 A1 | 1/2003 | |
| WO | WO-2012109152 A1 * | 8/2012 | ........... A61K 31/192 |
| WO | WO 2013/108254 A1 | 7/2013 | |
| WO | 2017/140422 A1 | 8/2017 | |
| WO | 2017/140430 A1 | 8/2017 | |
| WO | WO 2017/202496 A1 | 11/2017 | |

OTHER PUBLICATIONS

Khan et al., "Luminol-based chemiluminescent signals: clinical and non-clinical application and future uses," Appl Biochem Biotechnol. May 2014;173(2):333-55. (Year: 2014).*
Sestok, "The Heat of Reaction of Luminol: Energy Flow in a Chemiluminescent Reaction," SOAR Research Proposal (2015). (Year: 2015).*
Phosphal 75 SA Brochure. (Year: 2007).*
Skripnikova Tatiana A et al: "Physico-chemical properties of isomeric forms of luminol in aqueous solutions", Journal of Molecular Structure, vol. 1154, Oct. 3, 2017 (Oct. 3, 2017), pp. 59-63, XP085285512.
International Search Report and Written Opinion mailed Mar. 28, 2019 in corresponding International Application No. PCT/EP2019/000012.
Chinese Office Action Corresponding to 201980008025.7 mailed Aug. 22, 2023.
Indonesian Office Action Corresponding to P00202005713 mailed Aug. 24, 2023.
New Zeland Office Action Corresponding to 764957 mailed Jan. 31, 2024.

* cited by examiner

*Primary Examiner* — Jared Barsky
(74) *Attorney, Agent, or Firm* — Finch & Maloney PLLC

(57) ABSTRACT

The present invention relates to a method for solubilizing 5-amino-2,3-dihydro-1,4-phthalazinedione or salts thereof, to the solubilisate produced by this method and respective uses in pharmaceutical dosage forms. A phosphatidylcholine-based solubilization method is disclosed.

8 Claims, No Drawings

METHOD FOR SOLUBILIZING 5-AMINO-2,3-DIHYDRO-1,4-PHTHALAZINEDIONE

CROSS-REFERENCE TO RELATED APPLICATIONS

This application is the National Stage entry under 35 U.S.C. § 371 of International Application No. PCT/EP2019/000012 filed on Jan. 10, 2019, published on Jul. 18, 2019, under Publication Number WO 2019/137825 A1, which claims the benefit of priority under 35 U.S.C. § 119 of European Patent Application Number 18000019.2 filed on Jan. 11, 2018, the entireties of which are herein incorporated by reference.

The present invention relates to a method for solubilizing 5-amino-2,3-dihydro-1,4-phthalazinedione or salts thereof, to the solubilisate produced by this method, uses thereof and a pharmaceutical composition containing said solubilisate.

Since decades, 5-amino-2,3-dihydro-1,4-phthalazinedione (luminol) is used by crime scene investigators to detect traces of blood, even if someone has tried hard to clean or remove it (cf. Barni et al., Talanta 2007, 72, 896-913). The intense luminescence upon oxidation catalyzed by the iron in hemoglobin renders luminol a sensitive sensor. Beside its forensic use, numerous other applications ranging from environmental to medical have been established since the first report on the synthesis of luminol had appeared (A. J. Schmitz, Über das Hydrazid der Trimesinsäure und der Hemimellithsäure, Heidelberg, 1902). For instance, luminol is used for heavy metal detection or biosensing in bioanalytical chemistry (cf. Klopf and Nieman, Anal. Chem. 1983, 55, 1080-1083).

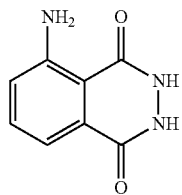 [SMILES: Nc1cccc2c(=O)[nH][nH]c(=O)c12]

Alkaline salts of luminol have been structurally characterized only recently (Guzei et al., J. Coord. Chem. 2013, 66, 3722-3739), as the sodium salt of luminol has regained interest for its pharmaceutical activity. Na-luminolate shows great potential in immunomodulatory treatment of inflammatory and autoimmune diseases. Moreover, Na-luminolate shows a rich polymorphism with three anhydric crystal structures characterized so far (cf. WO 2011/107295 A1; WO 2016/96143 A1). Also for luminol itself two crystalline forms have been disclosed (Paradies, Ber. Bunsen-Ges. Phys. Chem 1992, 96, 1027-1031; WO 2017/140430 A1). General physico-chemical properties of isomeric forms of luminol in aqueous solutions have been disclosed by Skripnikova et al. (2017; J Mol Struct 1154: 59-63). Special therapeutic uses for these Na-luminolate or luminol crystalline forms have been described in WO 2017/202496 A1.

It is known that crystalline forms of a compound may display differing physical characteristics such as solubility, dissolution rate and stability (cf. Haleblian und McCrone (1969): Journal of Pharmaceutical Sciences, 58:911-929). These properties can influence the pharmaceutical processing of a compound as well as its bioavailability and pharmacokinetics and thus its biologic efficacy (cf. Griesser (2006) in: Polymorphisms in the Pharmaceutical Industry. Hilfiker (Ed.) 211-234). A formulation for increasing the oral bioavailability of drugs by adding at least one piperine to the solution was disclosed in WO 2013/108254 A1.

While the luminol salts described hitherto are readily soluble in water luminol itself is only poorly water-soluble. Moreover, the small amount that can be solved tends to precipitate after a few days. Also a sensitivity to light, high temperature and metal cations has been described. This hampers seriously the use of aqueous luminol solutions. The problem may be overcome by using a basic solution, or by using a diluent like ethanol or DMSO. These diluents, however, are not acceptable for a broad variety of pharmaceutical applications.

The use of luminol sodium salt is advantageous in regard to solubility in an aqueous environment. For the absorption in the gastrointestinal tract, topical applications for transdermal delivery or for a transport across the blood-brain barrier, however, it would be preferable if the free acid could be administered in order to increase the bioavailability of luminol. Thus sufficiently high plasma and intracellular concentrations could be reached for maxing out the therapeutic potential of luminol. Thus there is a need to find a method for solubilizing luminol in an aqueous medium.

There is a variety of approaches for improving the solubility of lipophilic pharmaceutical agents and in many cases also their bioavailability by using solubilization techniques. Herein the solubility of an agent in a medium is augmented by adding a third substance. These third substances are referred to as solubilizers (solubilizing agents), substances that may for example build a complex with the substance to be solubilized. Examples for such chelating agents are sodium benzoate and sodium salicylate. Another mechanism of action of solubilizers is the augmentation of the dissolving capacity of the solvent, for example by disturbing the cluster structure of water. Examples for such structure breakers are glycerol (glycerin) and macrogols (polyethylene glycol, PEG).

A third solubilization mechanism are micelle and liposome application technologies. They have won broad attention throughout the last decades. Herein the substance to be delivered is enclosed in a spherical aggregate of surfactant molecules. These molecules are characterized by a polar head group and a long nonpolar chain ("tail"). When given into an aqueous medium these molecules tend to associate by aggregating to spherical structures by orienting the polar head group towards the surrounding medium and the nonpolar chain towards the interior of the spheres. When these spheres consist of only one layer of such amphiphilic molecules they are referred to as micelles. Depending on the nature of the amphiphilic molecule and the reaction conditions it is also possible to form spheres with more than one layer. Herein a second layer is formed inside the outer layer of the sphere, the nonpolar groups of this second layer being oriented towards the nonpolar groups of the outer layer, and the polar head groups being oriented towards the interior of the sphere. Such aggregates are referred to as liposomes. In their structure they resemble the lipid bilayer of the cell membrane. There are also multi-layered liposomes in which at least two liposomal spheres are formed concentrically around one another, thus building a multispherical aggregate. When given in a lipophilic medium these substances tend to build inversed spherical structures where the lipophilic chain is oriented towards the solution medium and the other layers are arranged accordingly.

Different uses of such loaded spheres have been described in the art, among them the usage as a dosage form for the application of lipophilic substances and/or for increasing the bioavailability of the enclosed substance. In micelles, the enclosed nonpolar substance concentrates in the interior space of the sphere toward which the nonpolar chains of the amphiphilic molecules are oriented. In liposomes, however, the interior space of the spheres is an aqueous, respectively hydrophilic medium. It can serve for packaging hydrophilic molecules. Poorly water-soluble, respectively lipophilic molecules, however, gather mostly in between the lipophilic structures of the liposomal layers.

Micelle-based solubilization techniques have been disclosed for example in WO 03/007907 A1 or WO2014/094921 A1. Therein an emulsifier with a HLB (hydrophilic-lipophilic balance) value of 9-16 or 13-18 is used, respectively. Polysorbate (Tween) 20 or 80 is often used. The implementation of this technology is apparently limited to the production of chewing gum.

A further approach is the admixture of a glucuronidation inhibitor to the pharmaceutical composition. Surfactants such as poloxamers or polysorbate 20, polysorbate 60, polysorbate 80 are widely used. Another common glucuronidation inhibitor is bioperine. Glucuronidation inhibitors, however, inhibit also the proper metabolization and consequently the elimination of other drugs or endogenous substances. Thus their use is a double-edged sword and should depend on the medication of each individual patient. Therefore such a composition might bear problems for a long-term medication, in particular in multimorbid patients.

From empiric pharmacokinetic measurements it is known that the organism can absorb micelles as well as liposomes in the gastrointestinal tract via the intestinal villi. However, their degree of absorption seems to be rather variable and therefore these methods have met a mixed success for augmenting the bioavailability of the enclosed compound. The transport, respectively the absorption rate over the cell membrane is an intrinsic characteristic for each substance, depending on a variety of factors such as molecule size, degree of lipophilicity and the presence of suitable transporter molecules inside the cell membrane. For many compounds these parameters are not known and would have to be determined first before finding a suitable packaging for this specific compound.

Liposomal applications have been widely discussed in medicine and pharmacology and some sophisticated solutions have been developed for specific active agents. Their use, however, is not very common. One reason are the relatively high production costs, another reason are possible adverse side effects. A liposome-based self-emulsification method for poorly water-soluble dietary supplements and pharmaceutic active agents was disclosed in EP 3290026 A1. In particular, when parenterally applied, liposomes carry the risk of accumulating in the liver, the spleen and/or the bone marrow. Therefore, liposomal formulations are often viewed skeptically.

A nano-liposphere-based formulation method for increasing drug bioavailability was disclosed in WO 2013/108254. Although this method offers some advancement over the state-of-the-art there are also some inherent drawbacks. High-pressure homogenizers are needed for the production of these solid lipid nanoparticles. However, high-pressure induced drug degradation has been described for some drugs or dietary supplements. Lipid crystallization, gelation phenomena and co-existence of several colloidal species occur. Further restrictive factors such as cytotoxic effects after phagocytosis, toxic effects of organic residues and a difficult industrial scale-up have limited their use until now (Mehnert and Mäder, Adv Drug Deliv Res 2001, 47, 165-196; Dudala et al., Int J Pharm Investg 2014, 4, 149-155). Moreover, their drug loading capacity is relatively small and they display a low viscosity. This makes them not very attractive for topic or transdermal application forms (Mukherjee et al., Indian J Pharm Sci 2009, 71, 349-358). Further, the use of an amphiphilic solvent such as lower alkyl esters of lactic acid or N-methylpyrrolidone is required in WO 2013/108254. N-methylpyrrolidone is listed as a substance of very high concern in respect of being potentially carcinogenic and toxic for reproduction, methyl lactate is usually hydrolyzed to lactate and methanol in an aqueous environment. Ethyl lactate etc. is well tolerated. However due to relatively high production costs it is not a very attractive solvent.

A solubilization technique for ubichinon $Q_{10}$ by means of triglyceride-containing light oil was described in WO 03/007907 A1.

Another solubilization technique is the formation of inclusion complexes of the substance to be solubilized with cyclodextrins such as α-, β- or γ-cyclodextrin or cyclodextrin derivatives such as 2-hydroxypropyl-β-cyclodextrin, methyl-β-cyclodextrin or trimethyl-β-cyclodextrin. Typically, cyclodextrins are composed of 6 to 8 1,4-linked α-D-glucopyranosides forming macrocycles. Thus a water-soluble toroid (cone-shaped or bucket-shaped) structure is generated which is capable to host hydrophobic substances in its interior. The interior space is considerably less hydrophilic than the outside contacting the aqueous environment. Cyclodextrins are produced from starch by enzymatic treatment. They are loaded with the compound to be solubilized by dispersion. The compound to be solubilized can then be released by contacting these complexes with water, by pH or temperature changes, depending on the specific composition. However, the development of cyclodextrin is apparently not easy and relatively costly. This limited their use until now. A further problem is that cyclodextrins interact with preservatives such as parabens.

Thus, all these techniques have their advantages but also some drawbacks.

Polysorbates are widely used in these solubilization techniques. However, there is an ongoing controversy about a detrimental impact of polysorbates on health. Polysorbate-20 is discussed to be contaminated with unreacted 1,4-dioxane and ethylene oxide (at least from some suppliers). These are known skin-permeable carcinogenic substances (cf. http://www.fda.gov/ohrms/dockets/98fr/060199a.txt, as of Mar. 22, 2017). Polysorbate 80 was recently found to have detrimental effects on murine gut microbiota, thus promoting obesity and inflammatory bowel diseases (Chassaing et al., Dietary emulsifiers impact the mouse gut microbiota promoting colitis and metabolic syndrome, Nature, 2015, 519, 92-96). This is of particular importance for patients with chronic inflammatory bowel diseases (IBD) such as Crohn's disease (Roberts et al., Translocation of Crohn's disease *Escherichia coli* across M-cells: contrasting effects of soluble plant fibres and emulsifiers, Gut, 2010, 59, p. 1331-1339). IBD are a target indication for the therapeutic use of 5-amino-2,3-dihydro-1,4-phthalazinedione. A further problem of polysorbates such as Tween 80 is that they reduce the efficacy of widely used preservatives such as parabens by binding them (cf. Blanchard et al., Effect of sorbitol on interaction of phenolic preservatives with polysorbate 80, 1977, J Pharm Sci 66, p. 1470-1473). The paraben concentration, however, should not be increased accordingly because of their estrogenic potential (cf. Okubo et al.; ER-dependent estrogenic activity of parabens assessed by proliferation of human breast cancer MCF-7 cells and expression of ERalpha and PR; 2001, Food Chem Toxicol 39, p. 1225-1232). Other well-known problems of polysorbates (in particular polysorbate 80) are hypersensitivity reactions of patients (cf. Steele et al., Hypersensitivity reactions to the polysorbate contained in recombinant erythropoietin and darbepoietin, Nephrology, 2005, 10, p. 317-320; Norris et al., Polysorbate 80 hypersensitivity reactions: a renewed call to action, Commun Oncol, 2010, 7, 425-428). Polysorbate 80 has also been associated with systemic hypotension in amiodarone formulations where this may even lead to casualties (cf. Cushing et al., PM 101: A cyclodextrin-based intravenous formulation of amiodarone devoid of adverse hemodynamic effects, Eur J Pharmacol, 2009, 607, p. 167-172).

A solubilization method for 5-amino-2,3-dihydro-1,4-phthalazinedione should fulfil the following criteria:
easy-to-handle
no lengthy development time for finding a favorable composition
no costly equipment needed
inexpensive materials and production costs
no addition of polysorbate (Tween) solubilizers needed.

Surprisingly, it was found that the method according to the invention is able to solve this task.

Herein, 5-amino-2,3-dihydro-1,4-phthalazinedione is solubilized by the method according to the invention, comprising the following steps:
a) Providing 5-amino-2,3-dihydro-1,4-phthalazinedione in the overall range of 0.1% to 25% per weight at room temperature and a pressure of 0.2 bar to 1 bar;
b) Adding in any sequence the solubilization agents of at least one phosphatidylcholine in the overall range of 20% to 80% per weight,
at least one medium-chained triglyceride in the overall range of 10% to 70% per weight,
at least one lysophosphatidylcholine in the overall range of 1% to 15% per weight,
at least one $C_2$ to $C_4$ alcohol in the overall range of 1% to 20% per weight, and at least one of glyceryl stearate and/or a saturated or unsaturated $C_{14}$ to $C_{20}$ fatty acid in the overall range of 0.5% to 10% per weight, respectively,
wherein the relative weight percentages of all ingredients add up to 100% and all solubilization agents are pharmaceutically acceptable excipients;
c) Cautiously heating the resulting mixture by continuously increasing the temperature with a continuous temperature increment of 0.5° C./min-3° C./min over a period of 20-60 minutes;
d) Stopping the temperature increase in a temperature range of 30° C. to 125° C. as soon as a clear solution is reached; and
e) Letting the resulting solubilisate cool down to room temperature.

In a preferred embodiment, the 5-amino-2,3-dihydro-1,4-phthalazinedione is solubilized by the method according to the invention, comprising the following steps:
a) Providing 5-amino-2,3-dihydro-1,4-phthalazinedione in the overall range of 0.5% to 10% per weight at room temperature and a pressure of 0.2 bar to 1 bar;
b) Adding in any sequence the solubilization agents of at least one phosphatidylcholine in the overall range of 20% to 80% per weight,
at least one medium-chained triglyceride in the overall range of 10% to 70% per weight,
at least one lysophosphatidylcholine in the overall range of 1% to 15% per weight,
at least one $C_2$ to $C_4$ alcohol in the overall range of 1% to 20% per weight, and at least one of glyceryl stearate and/or a saturated or unsaturated $C_{14}$ to $C_{20}$ fatty acid in the overall range of 0.5% to 10% per weight, respectively,
wherein the relative weight percentages of all ingredients add up to 100% and all solubilization agents are pharmaceutically acceptable excipients;
c) Cautiously heating the resulting mixture by continuously increasing the temperature with a continuous temperature increment of 0.5° C./min-3° C./min over a period of 20-60 minutes;
d) Stopping the temperature increase in a temperature range of 30° C. to 125° C. as soon as a clear solution is reached; and
e) Letting the resulting solubilisate cool down to room temperature.

Another aspect of the invention is that the method according to the invention does not need polysorbates as solubilizers and/or emulsifiers. Therefore 5-amino-2,3-dihydro-1,4-phthalazinedione can be solubilized by the method according to the invention, comprising the following steps:
a) Providing 5-amino-2,3-dihydro-1,4-phthalazinedione in the overall range of 0.1% to 25% per weight at room temperature and a pressure of 0.2 bar to 1 bar;
b) Adding in any sequence the solubilization agents of at least one phosphatidylcholine in the overall range of 20% to 80% per weight,
at least one medium-chained triglyceride in the overall range of 10% to 70% per weight,
at least one lysophosphatidylcholine in the overall range of 1% to 15% per weight,
at least one $C_2$ to $C_4$ alcohol in the overall range of 1% to 20% per weight, and at least one of glyceryl stearate and/or a saturated or unsaturated $C_{14}$ to $C_{20}$ fatty acid in the overall range of 0.5% to 10% per weight, respectively,
wherein the relative weight percentages of all ingredients add up to 100% and all solubilization agents are pharmaceutically acceptable excipients;
c) Cautiously heating the resulting mixture by continuously increasing the temperature with a continuous temperature increment of 0.5° C./min-3° C./min over a period of 20-60 minutes;
d) Stopping the temperature increase in a temperature range of 30° C. to 125° C. as soon as a clear solution is reached; and
e) Letting the resulting solubilisate cool down to room temperature,
characterized in that the resulting solubilisate is devoid of polysorbate.

In further embodiments the solubilisates according to the invention can also be produced from salts of 5-amino-2,3-dihydro-1,4-phthalazinedione. Sodium, potassium and lithium salts have been described for therapeutic applications (cf. WO 2010/082858). Crystal structures for lithium, sodium, potassium, rubidium and cesium salts were described in Guzei et al. (2013, Journal of Coordination Chemistry 66, 3722-3739; see also WO 2011/107295 A1; WO 2016/96143 A1). In general, these salts are water-soluble and therefore don't need to be solubilized for aqueous solutions. However, when used therapeutically, the solubilisates according to the invention are apt to prolong the shelf life of liquid dosage forms. In liquid dosage forms for oral administration they can cover the taste of 5-amino-2,3-dihydro-1,4-phthalazinedione sodium salt solutions which is not appealing for many patients. Moreover, they improve the resorption of these salts of 5-amino-2,3-dihydro-1,4-phthalazinedione from the gastrointestinal tract in respect of amount and time. Herewith, the bioavailability can be improved what might lead to favorable pharmacokinetic properties. Larger ion concentrations, however, hamper the formation of multilamellar vesicles which are thought to be essential for solving the solubilisates according to the invention in an aqueous solution. Therefore, the maximal relative amounts of 5-amino-2,3-dihydro-1,4-phthalazinedione salts is lower than for the free base.

It was found that maximally 2 weight-% of 5-amino-2,3-dihydro-1,4-phthalazinedione salts can be solved according to the inventive method.

Thus, a salt of 5-amino-2,3-dihydro-1,4-phthalazinedione is solubilized by the method according to the invention, comprising the following steps:
  a) Providing a salt of 5-amino-2,3-dihydro-1,4-phthalazinedione in the overall range of 0.1% to 2% per weight at room temperature and a pressure of 0.2 bar to 1 bar, wherein the salt is a sodium, potassium or lithium salt or mixtures thereof;
  b) Adding in any sequence the solubilization agents of at least one phosphatidylcholine in the overall range of 20% to 80% per weight,
    at least one medium-chained triglyceride in the overall range of 10% to 70% per weight,
    at least one lysophosphatidylcholine in the overall range of 1% to 15% per weight,
    at least one $C_2$ to $C_4$ alcohol in the overall range of 1% to 20% per weight, and at least one of glyceryl stearate and/or a saturated or unsaturated $C_{14}$ to $C_{20}$ fatty acid in the overall range of 0.5% to 10% per weight, respectively,
    wherein the relative weight percentages of all ingredients add up to 100% and all solubilization agents are pharmaceutically acceptable excipients;
  c) Cautiously heating the resulting mixture by continuously increasing the temperature with a continuous temperature increment of 0.5° C./min-3° C./min over a period of 20-60 minutes;
  d) Stopping the temperature increase in a temperature range of 30° C. to 125° C. as soon as a clear solution is reached; and
  e) Letting the resulting solubilisate cool down to room temperature.

In preferred embodiments also the embodiments of these salts of 5-amino-2,3-dihydro-1,4-phthalazinedione are characterized in that the resulting solubilisate is devoid of polysorbate.

It is understood that the following descriptions and embodiments refer likewise to said salts of 5-amino-2,3-dihydro-1,4-phthalazinedione as for the free base.

Confusing and even contradictory definitions can be found in the art. In order to avoid any ambiguity a solubilisate according to the invention is defined as follows:

A solubilisate is the composition of 5-amino-2,3-dihydro-1,4-phthalazinedione or of one of its salts or a mixture thereof and the solubilizing agents as defined according to the invention. Further addition of a solvent or diluent shall not be covered by this term. The solubilisate according to the invention is produced first by the solubilization method according to the invention, then a specific pharmaceutical composition is produced with said solubilisate, and finally said pharmaceutical composition is packaged into a suitable pharmaceutically acceptable container for the respective dosage form.

The solubilisate according to the invention is characterized by the substantially complete solubilization of 5-amino-2,3-dihydro-1,4-phthalazinedione or of one of its salts or a mixture thereof, thus being a nearly perfect solution in which the molecules behave substantially as independent entities in a solution and substantially undergo the distribution and thermodynamic rules of Brownian motion. Thus the solubilisate is a clear solution containing 5-amino-2,3-dihydro-1,4-phthalazinedione or of one of its salts or a mixture thereof in a high concentration. In general, the solubilisate is not meant for administration without dilution, respectively to be administered without being formulated in a pharmaceutically acceptable dosage form. In most cases, a portioned solubilisate accounts to a volume of a few ml.

In the scope of this patent application the terms "solubilization aggregate" or "solubilization essence" shall be used synonymously to "solubilisate".

A solubilisate according to the invention must be differentiated from a suspension (colloidal suspension). This term defines a heterogeneous mixture containing solid particles that sooner or later will undergo sedimentation. It is also different from an emulsion (a mixture of two liquids which usually are immiscible).

For increasing the bioavailability of a substance the complete solubilization is highly preferably.

The term solubilisate used according to the invention must be differentiated from the pharmaceutical composition. A pharmaceutical composition according to the invention is generated by diluting the solubilisate according to the invention in a preferably aqueous solution in order to produce a liquid dosage form, or by admixing the solubilisate to a topical dosage form, a capsule or a suppository.

A diluent in the scope of the present application is a diluting agent (dilutant, thinner). It is not part of the solubilisate according to the invention.

In the scope of the present application the term "solubilizing agent" refers to any chemical substance that is added to 5-amino-2,3-dihydro-1,4-phthalazinedione or of one of its salts or a mixture thereof in order to solubilize it so that 5-amino-2,3-dihydro-1,4-phthalazinedione or of one of its salts or a mixture thereof can be solved thereupon in an aqueous solution. The term "solubilizer" shall be used synonymously.

In the scope of the present application the term "medicine" shall comprise human and veterinary medicine.

A great advantage of such a solubilisate consists in its small volume. Thus it can be easily portioned to patient-friendly units, or relatively huge amounts of solubilized substance can be shipped at low costs. In order to produce a dosage form the preparation can be easily carried out by medical staff or patients.

The solubilisate according to the invention must be also be differentiated from a concentrate. A concentrate is a compound, respectively a composition of compounds without a diluent. Upon release of a concentrate into a diluent the concentrate dissolves itself either completely in the diluent or forms a suspension or emulsion with the diluent. A concentrate does not need the interaction with solubilizing agents, as it is intrinsically solvable in water or an aqueous solution.

In a preferred embodiment of the method according to the invention 5-amino-2,3-dihydro-1,4-phthalazinedione is provided in the overall range of 2% to 15% per weight, in a more preferred embodiment in the overall range of 2% to 10% per weight.

Phosphatidylcholines are a class of phospholipids linked to choline. They are a major component of cell membranes and are for example obtained from egg yolk, ox liver, marine animals, krill oil or soybeans. In practice, it showed that the origin of phosphatidylcholines influences their biological and chemical effects considerably. According to the invention the at least one phosphatidylcholine (PC) can be selected from the group comprising 1-palmitoyl-2-oleoyl-sn-glycero-3-phosphocholine (POPC), natural (non-hydrogenated) or hydrogenated soy bean PC, natural or hydrogenated egg PC, dipalmitoyl phosphatidylcholine (DPPC), dimyristoyl phosphatidylcholine (DMPC) or 1,2-dioleyl-SN-glycero-3-phosphocholine (DOPC), 1-oleoyl-palmitoyl phosphatidylcholine (OPPC), diasteroyl phosphatidylcholine (DSPC), monostearoylphosphatidylcholine (MSPC), diarachidoylphosphatidylcholine (DAPC), and mixtures thereof. Preferred phosphatidylcholines are non-hydrogenated soybean PC, DMPC, POPC and DOPC. Preferred are also non-hydrogenated phosphatidylcholines. Particularly preferred is non-hydrogenated soybean PC.

For topical dosage forms of a solubilisate according to the invention non-hydrogenated phosphatidylcholines are particularly preferred.

Lecithin is commonly used as a synonym for phosphatidylcholines. It is a mixture of phosphatidylcholine and other compounds.

According to the method of the invention phosphatidylcholines are used in the overall range of 20% to 80% per weight, preferred 40% to 70% per weight, more preferred 50% to 65% per weight and most preferred 60% per weight.

Medium-chained triglycerides (MCT) refer to triglycerides whose fatty acids have an aliphatic tail of 6-12 carbon atoms. Fatty acids incorporated in MCT are called medium-chain fatty acids (MCFA). In triglycerides three fatty acid molecules are bound to a glycerol backbone. Per definition, in MCT at least two of these three fatty acids must be MCFAs. According to the invention MCFA can be selected independently from one another from the group comprising caproic acid, enanthic acid, caprylic acid, pelargonic acid, capric acid, undecilyc acid, lauric acid, their unsaturated derivatives, and mixtures thereof. Preferred MCFA are caproic acid, caprylic acid, capric acid, and lauric acid.

It can be advantageous in some embodiments of the invention to use triglycerides containing 1 to 3 myristic acid and/or palmitic acid residues instead of MCFAs. Hence, these two fatty acids shall be subsumed under the term MCT according to the invention too.

MCT oils or MCT fats are oils or fats containing predominantly said MCT. These terms refer to a respective mixture of different MCT that may contain a variety of MCFA. According to the invention any reasonable mixing ratio shall be covered by these terms. MCT fats are often extracted from specific plant fats, while MCT oils do not occur naturally. MCT oils and MCT fats are broadly marketed as a healthy dietary supplement, respectively as a surrogate for long-chain fats in nutrition.

According to the method of the invention MCT are used in the overall range of 10% to 70% per weight, preferred 20% to 40% per weight, more preferred 25% to 35% per weight and most preferred 30% per weight.

Lysophosphatidylcholines (LPC, ysoPC, also: lysolecithins) are a class of derivatives of phosphatidylcholines, resulting of their partial hydrolysis in which one of the fatty acid groups is removed. In the organism this hydrolysis is effected by the enzyme phospholipase A2. According to the invention the at least one lysophosphatidylcholine can be selected independently from one another from the group comprising all hydrolyzed compounds of the phosphatidylcholines listed above, 1-lysophosphatidylcholines (2-acyl-sn-glycero-3-phosphocholines), 2-lysophosphatidylcholines, L-alpha-lysophosphatidylcholine, and mixtures thereof.

According to the method of the invention lysophosphatidylcholines are used in the overall range of 1% to 15% per weight, preferred 3% to 8% per weight, more preferred 5% to 7% per weight and most preferred 6% per weight.

In the scope of the present application said lysophosphatidylcholines are not a mere variant or substitute for phosphatidylcholines but fulfill an independent role. Surprisingly, it was found that two solubilizing agents of similar but not identical chemical constitution can significantly improve the solubilizing effect, if used in an uneven ratio. According to the invention the ratio phosphatidylcholine to lysophosphatidylcholine is from 80:1 to 1.33:1, preferred 40:1 to 3:1, more preferred 25:1 to 5:1 and most preferred 20:1 to 8:1.

According to the invention the at least one $C_2$ to $C_4$ alcohol (lower alcohol) can be selected from the group comprising ethanol, propanol, isopropanol, butane-1-ol, butane-2-ol, isobutanol (2-methyl-1-propanol), ethylene glycol (ethane-1,2-diol), α-propylene glycol (propane-1,2-diol), β-propylene glycol (propane-1-3-diol), 1,2-butylene glycol (butane-1,2-diol), 1,3-butylene glycol (butane-1,3-diol), 1,4-butylene glycol (butane-1,4-diol), and diethylene glycol. Preferred is ethanol.

According to the method of the invention $C_2$ to $C_4$ alcohols are used in the overall range of 1% to 20% per weight, preferred 2% to 10% per weight, more preferred 3% to 8% per weight and most preferred 5% per weight.

Glyceryl stearate (glycerol monostearate, GMS) is an emulsifier. The flaky powder is also hygroscopic. GMS is used as thickening, emulsifying, anti-caking, anti-staling and preservative agent.

According to the invention the at least one saturated or unsaturated $C_{14}$ to $C_{20}$ fatty acid can be used instead of or in combination with glyceryl stearate. It can be selected from the group comprising myristic acid (14:0), pentadecanoic acid (15:0), palmitic acid (16:0), heptadecanoic acid (17:0), stearic acid (18:0), nonadecanoic acid (19:0), arachidic acid (20:0), myristoleic acid (14:1,cis-$\Delta^9$), palmitoleic acid (16:1, cis-$\Delta^9$), sapienic acid (16:1, cis-$\Delta^6$), hexadecatrienoic acid (16:3, (n-3), oleic acid (18:1, cis-$\Delta^9$), elaidic acid (18:1, trans-$\Delta^9$), vaccenic acid (18:1, trans-$\Delta$), linoleic acid (18:2; cis,cis-$\Delta^9,\Delta^{12}$), linoleadic acid (18:2, trans,trans-$\Delta^9,\Delta^{12}$), A-linolenic acid (18:3, cis,cis,cis-$\Delta^9,\Delta^{12},\Delta^{15}$), γ-linolenic acid (18:3, (ω-3)), calendic acid (8E,10E,12Z-octadecatrienoic acid), stearidonic acid (18:4 (n-3)), dihomo-γ-linolenic acid (20:3; (ω-6)), eicosadienoic acid (20:2, (n-6)), eicosatrienoic acid (20:3, (n-3)), eicosatetraenoic acid (20:4, (n-3)), arachidonic acid (20:4, cis,cis,cis,cis-$\Delta^5,\Delta^8,\Delta^{11},\Delta^{14}$), eicosapentaenoic acid (20:5, cis,cis,cis,cis-$\Delta^5,\Delta^8,\Delta^{11},\Delta^{14},\Delta^{17}$). Preferred are even-numbered $C_{14}$ to $C_{20}$ fatty acids. Particularly preferred is oleic acid.

According to the method of the invention glyceryl stearate and/or a saturated or unsaturated $C_{14}$ to $C_{20}$ fatty acid are used in the overall range of 0.5% to 10% per weight, preferred 1% to 8% per weight, more preferred 2% to 6% per weight and most preferred 3% per weight.

The method according to the invention is usually started at room temperature. However, in alternative embodiments it may be also possible to preheat 5-amino-2,3-dihydro-1,4-phthalazinedione and/or any of the solubilizing agents to be added in step b) of the inventive method, provided that the preheating temperature does not exceed 28° C.

The method according to the invention can be performed at a pressure of 0.2 bar to 1 bar. It is preferred, however, to run the method at 1 bar (atmospheric pressure). For certain applications it may be preferable to use a light vacuum. The technical equipment for applying, maintaining and controlling such a light vacuum is well known in the art.

According to the method of the invention the resulting mixture is cautiously heated in step c) by continuously increasing the temperature over a period of 20-60 minutes. In preferred embodiments this period is 25-40 minutes, and most preferred 30-35 minutes.

An essential feature of the method according to the invention is the temperature control (temperature increment per time and duration of the heating). While there is a variability in the relative amounts of the solubilizing agents the controlled temperature increase is essential. Apparently, there is an optimal window for each substance to be solubilized, in dependence of the used mixture of solubilizing agents. The exact values are difficult to predict, they have to be found out empirically.

The continuous temperature increment (the steepness of the temperature ramp) can vary between 0.5° C./min to 3° C./min, preferred 1° C./min to 2° C./min and most preferred 2° C./min.

According to step d) the temperature increase is stopped in a temperature range of 30° C. to 125° C. as soon as a clear solution is reached. This moment depends heavily on the selected solubilization agents and reaction conditions. Apparently, it is not possible to foretell this "solubilizing temperature" on the basis of the specific components that are going to be used. Each composition of these components displays specific characteristics which have to be found out experimentally. Thus it becomes to the experimenter to find out the optimal combination of these parameters.

It is understood that the method according to the invention can be varied in such a way that any of the solubilizing agents of step b) can be provided first and then 5-amino-2,3-dihydro-1,4-phthalazinedione or of one of its salts or a mixture thereof well as the other solubilizing agents can be added in any sequence. It is also possible to provide a mixture of the solubilizing agents of step b) first and then add 5-amino-2,3-dihydro-1,4-phthalazinedione or of one of its salts or a mixture thereof. This variation was found to be neutral to the outcome of the method according to the invention.

In a preferred embodiment said mixture of the solubilizing agents of step b) and 5-amino-2,3-dihydro-1,4-phthalazinedione or of one of its salts or a mixture thereof are provided in a two-compartment system. This may facilitate the solubilization process according to the invention and each compartment can be marketed separately. This can be advantageous for the stability and thus for the shelf life of the dosage form according to the invention.

The moment when the resulting solubilisate has become a clear solution is determined by observation of the experimenter. In general, this moment is achieved when the solution appears transparent and does not display any sedimentation, precipitation, slurs, smears or striping (zebra effect).

In an alternative embodiment the parameters for the temperature ramp according to the invention that have been determined as described before can be implemented in an automatized or half-automatized device setting. This may be advantageous, for example, in an upscale industrial application.

The solubilisates produced according to the method of the invention maintain this clearness upon cooling down and stay clear and stable upon being stored. The achievable storage time of a pharmaceutical dosage form containing said solubilisate (roughly corresponding to the shelf life of a product) is apparently not limited. In preliminary stability analyses the minimum storage time was never less than 6 months.

However, for augmenting the shelf life of these solubilisates of 5-amino-2,3-dihydro-1,4-phthalazinedione or of one of its salts or a mixture thereof at least one antioxidant can be added to the solubilisate. In preferred embodiments this at least one antioxidant is a pharmaceutically acceptable excipient. Suitable antioxidants can be selected from the group comprising lactic acid, ascorbic acid, sodium ascorbate, calcium ascorbate, potassium ascorbate, fatty acid esters of ascorbic acid, ascorbyl palmitate, ascorbyl stearate, tocopherols, alpha-tocopherol, beta-tocopherol, gamma-tocopherol, delta-tocopherol, alpha-tocotrienol, beta-tocotrienol, gamma-tocotrienol, delta-tocotrienol, propyl gallate, octyl gallate, dodecyl gallate, ethyl gallate, guaiac resin, erythorbic acid, sodium erythorbate, erythorbin acid, sodium erythorbin, tert-butylhydroquinone, butylated hydroxyanisole, butylated hydroxytoluene, mono-, di-, trisodium phosphate, mono-, di-, tripotassium phosphate, anoxomer, ethoxyquin, potassium lactate, stannous chloride, sodium thiosulfate, 4-hexylresorcinol, glucose oxidase. Preferred are ascorbyl palmitate and alpha-tocopherol, beta-tocopherol, gamma-tocopherol, delta-tocopherol. Particularly preferred is a combination of ascorbyl palmitate and at least one of alpha-tocopherol, beta-tocopherol, gamma-tocopherol, delta-tocopherol.

The term tocopherol(s) refers to any of the aforementioned tocopherols or a mixture thereof.

According to the method of the invention this at least one antioxidant can be optionally added to said solubilisate or its preferred embodiments in the overall range of 0.01% to 10% per weight, preferred 0.1% to 5% per weight, more preferred 0.2% to 1% per weight and most preferred 0.3% to 0.5% per weight.

Thus the present application refers also to a solubilisate resulting from the solubilizing method according to the invention:

A solubilisate comprising 5-amino-2,3-dihydro-1,4-phthalazinedione in the range of 0.5% to 10% per weight and the following solubilization agents:
  a) at least one phosphatidylcholine in the overall range of 20% to 80% per weight;
  b) at least one medium-chained triglyceride in the overall range of 10% to 70% per weight;
  c) at least one lysophosphatidylcholine in the overall range of 1% to 15% per weight;
  d) at least one $C_2$ to $C_4$ alcohol in the overall range of 1% to 20% per weight, and
  e) and at least one of glyceryl stearate or a saturated or unsaturated $C_4$ to $C_{20}$ fatty acid in the range of 0.5% to 10% per weight, respectively, wherein the relative weight percentages of all ingredients add up to 100% and all solubilization agents are independently from one another pharmaceutically acceptable excipients.

In a preferred embodiment the solubilisate according to the invention comprises 5-amino-2,3-dihydro-1,4-phthalazinedione in the range of 1% to 8% per weight and
  a) at least one phosphatidylcholine in the overall range of 40% to 70% per weight;
  b) at least one medium-chained triglyceride in the overall range of 20% to 40% per weight;
  c) at least one lysophosphatidylcholine in the overall range of 3% to 8% per weight;
  d) at least one $C_2$ to $C_4$ alcohol in the overall range of 2% to 10% per weight, and
  e) and at least one of glyceryl stearate or a saturated or unsaturated $C_{14}$ to $C_{20}$ fatty acids in the range of 0.5% to 5% per weight, respectively, wherein the relative weight percentages of all ingredients add up to 100% and all solubilization agents are independently from one another pharmaceutically acceptable excipients.

In a further preferred embodiment the solubilisate according to the invention comprises 5-amino-2,3-dihydro-1,4-phthalazinedione in the range of 2% to 5% per weight and
  a) at least one phosphatidylcholine in the overall range of 40% to 60% per weight;
  b) at least one medium-chained triglyceride in the overall range of 25% to 35% per weight;
  c) at least one lysophosphatidylcholine in the overall range of 5% to 7% per weight;
  d) at least one $C_2$ to $C_4$ alcohol in the overall range of 4% to 7% per weight, and
  e) and at least one of glyceryl stearate or a saturated or unsaturated $C_{14}$ to $C_{20}$ fatty acids in the range of 0.5% to 5% per weight, respectively, wherein the relative weight percentages of all ingredients add up to 100% and all solubilization agents are independently from one another pharmaceutically acceptable excipients.

In alternative embodiments the method according to the invention refers also to:

A solubilisate comprising a 5-amino-2,3-dihydro-1,4-phthalazinedione salt in the range of 0.1% to 2% per weight and the following solubilization agents,
wherein said salt is a sodium, potassium or lithium salt or a mixture thereof, and
  a) at least one phosphatidylcholine in the overall range of 20% to 80% per weight;
  b) at least one medium-chained triglyceride in the overall range of 10% to 70% per weight;
  c) at least one lysophosphatidylcholine in the overall range of 1% to 15% per weight;
  d) at least one $C_2$ to $C_4$ alcohol in the overall range of 1% to 20% per weight, and
  e) and at least one of glyceryl stearate or a saturated or unsaturated $C_{14}$ to $C_{20}$ fatty acid in the range of 0.5% to 10% per weight, respectively, wherein the relative weight percentages of all ingredients add up to 100% and all solubilization agents are independently from one another pharmaceutically acceptable excipients.

According to the invention said solubilisate or its preferred embodiments may additionally contain an antioxidant as listed before in the overall range of 0.01% to 10% per weight, preferred 0.1% to 5% per weight, more preferred 0.2% to 1% per weight and most preferred 0.3% to 0.5% per weight.

In a particularly preferred embodiment of this solubilisate said at least one saturated or unsaturated $C_{14}$ to $C_{20}$ fatty acid is oleic acid.

In a particularly preferred embodiment of this solubilisate said at least one $C_2$ to $C_4$ alcohol is ethanol.

In preferred embodiments at least one antioxidant in the overall range of 0.01 to 10% per weight is contained additionally in the solubilisate according to the invention, wherein said at least one antioxidant is a pharmaceutically acceptable excipient.

In particularly preferred embodiments said at least one antioxidant is ascorbyl palmitate and/or at least one tocopherol.

Another aspect of the present application is a solubilisate according to the invention for prophylactic or therapeutic use in medicine as well as to the prophylactic or therapeutic use of said solubilisate in medicine.

In the scope of the present application the term "medicine" shall refer to human medicine as well as veterinary medicine.

In particular, the present application refers to the solubilisate according to the invention for prophylactic or therapeutic use as an immunomodulator.

The present application refers also to the use of a solubilisate according to the invention for treating conditions with an overshooting immune reaction or conditions with an immunodeficient background.

The present application refers also to a pharmaceutical composition for treating a medical condition, comprising a solubilisate according to the invention of 5-amino-2,3-dihydro-1,4-phthalazinedione or of one of its salts or a mixture thereof.

Herein the term permeability refers to the extent of absorption of a drug in humans across the intestinal wall. According to the established definition a drug is classified as highly permeable if 90% or more of the orally administered dose are resorbed in the gastrointestinal tract. Correspondingly, a drug having an absorption rate of less than 90% is classified as low permeable.

Thus solubility and permeability are intrinsic substance properties. Absorption and bioavailability, however, describe pharmaceutical parameters that may be improved by suitable measures. While resorption refers to the fraction from the orally applied substance amount that is absorbed from the gastrointestinal tract the bioavailability of a substance depends not only from resorption but also from species-specific protein binding in blood and from pharmacokinetic parameters such as first-pass metabolism.

Therefore another aspect of the invention is the prophylactic or therapeutic use of a solubilisate according to the invention for enhancing the absorption and/or bioavailability of 5-amino-2,3-dihydro-1,4-phthalazinedione or of one of its salts or a mixture thereof.

Thus, the present application refers also to a solubilisate according to the invention for use in a pharmaceutical dosage form.

Moreover, the present application refers also to the use in medicine of the solubilisate according to the invention in a pharmaceutical dosage form.

In most cases, the solubilisate of 5-amino-2,3-dihydro-1,4-phthalazinedione or of one of its salts or a mixture thereof is not yet a pharmaceutical dosage form. To be ready for intake in a liquid dosage form said solubilisate has to be solved in a diluent. The preferred diluent for liquid dosage forms is water. Therefor the solubilisate according to the invention is added to an aqueous solution in a suitable container. The container can be selected from a group comprising, but not limited to, bottles, vials, flacons, glasses, cups, syringes, jars, pots, dispensers, boxes, tubes, caps, sachets and custom-built two- or multiple-compartment containers. Preferred containers are bottles, vials and jars.

It is preferred that the container with the aqueous solution and the solubilisate solved therein is stirred or agitated several times to ensure a homogeneous distribution of the solubilisate in the aqueous solution.

Thus the present application refers also to a pharmaceutical dosage form, wherein a solubilisate according to the invention is solved in an aqueous solution.

In another preferred embodiment of the invention a solubilisate according to the invention is included in soft gelatin capsules (SGC). SGCs are dissolved on their passage through the gastrointestinal tract. They consist mainly of gelatin enriched with variable amounts of plasticizers such as glycerol or sorbitan. The release rate depends on the specific formulation of the SGC carrier material. They are also suitable for a sustained release of the active agent. SGCs are particularly useful for the administration of poorly water-soluble active agents. They are excellently suited to host a solubilisate of 5-amino-2,3-dihydro-1,4-phthalazinedione in a cavity.

In another embodiment of the invention a solubilisate according to the invention is provided in hard gelatin capsules. They consist of gelatin, water and usually a colorant, but they don't contain a plasticizer. A solubilisate according to the invention can be included during the production process. It will be released upon dissolution of the hard gelatin capsule.

In another preferred embodiment of the invention a solubilisate according to the invention is included in chewable tablets or hard caramels. Herein the solubilisate according to the invention is integrated into the matrix of the tablets or caramels.

In a further embodiment of the invention a solubilisate according to the invention is included in a suppository. In a typical production method waxes with a low melting point as well as a mixture of fatty acid glycerides such as cocoa butter are first melted. Then the active agent, herein a solubilisate of 5-amino-2,3-dihydro-1,4-phthalazinedione or of one of its salts or a mixture thereof, is homogenously dispersed under stirring or other mixing methods. The molten homogeneous mixture is then transferred to suitable molds and cooled down until solidification.

In yet another embodiment of the invention a solubilisate according to the invention is provided as a topical application form, such as creams, emulsions, lotions, gels, hydrogels, pastes, powders, ointments, liniment, films, liposomes, dermal patches, transdermal patches, transdermal sprays or suspensions.

In a further aspect the present application refers also to a pharmaceutical composition containing 5-amino-2,3-dihydro-1,4-phthalazinedione or of one of its salts or a mixture thereof formulated in a dosage form as defined before, and at least one pharmaceutically acceptable excipient.

The term "pharmaceutical excipients" refers to natural or synthetic compounds that are added to a pharmaceutical formulation alongside the pharmaceutical active agent. They may help to bulk up the formulation, to enhance the desired pharmacokinetic properties or the stability of the formulation, as well as be beneficial in the manufacturing process. Advantageous classes of excipients according to the invention include carriers, binding agents, lubricants, glidants, disintegrants, colorants, buffers, preservatives, emulsifiers, permeation enhancers, antioxidants, diluents, pH regulators, fatiquors, solvents, consistency enhancers, hydrotopes, sweeteners, acidifiers, thickening agents, antiadherents, fillers, flavors, sweeteners, opacifiers, flavoring substances and aromatic substances.

It can be advantageous, respectively mandatory to add one or more pharmaceutically acceptable carrier to a pharmaceutically active agent. Eligible are all carriers known in the art and combinations thereof. In solid dosage forms they can be for example plant and animal fats, waxes, paraffins, starch, tragacanth, cellulose derivatives, polyethylene glycols, silicones, bentonites, silica, talcum, zinc oxide. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethylglycols, fatty acid esters of sorbitan. Suspensions according to the invention may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth.

The term binding agents refers to substances that bind powders or glue them together, rendering them cohesive through granule formation. They serve as a "glue" of the formulation. Binding agents increase the cohesive strength of the provided diluent or filler.

Suitable binding agents are for example starch from wheat, corn, rice or potato, gelatine, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminium silicate, waxes and others. The percentage of the binding agent in the composition can range from 1-30% by weight, preferred 2-20% by weight, more preferred 3-10% by weight and most preferred 3-6% by weight.

Colorants are excipients that bestow a colorization to the composition of the drink, respectively the dosage form. These excipients can be food colorants. They can be adsorbed on a suitable adsorption means such as clay or aluminium oxide. The amount of the colorant may vary between 0.01 and 10% per weight of the pharmaceutical composition, preferred between 0.05 and 6% per weight, more preferred between 0.1 and 4% per weight, most preferred between 0.1 and 1% per weight.

Suitable pharmaceutical colorants are for example curcumin, riboflavin, riboflavin-5'-phosphate, tartrazine, alkannin, quinolione yellow WS, Fast Yellow AB, riboflavin-5'-sodium phosphate, yellow 2G, Sunset yellow FCF, orange GGN, cochineal, carminic acid, citrus red 2, carmoisine, amaranth, Ponceau 4R, Ponceau SX, Ponceau 6R, erythrosine, red 2G, Allura red AC, Indathrene blue RS, Patent blue V, indigo carmine, Brilliant blue FCF, chlorophylls and chlorophyllins, copper complexes of chlorophylls and chlorophyllins, Green S. Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminium, silver, gold, pigment rubine, tannin, orcein, ferrous gluconate, ferrous lactate.

Moreover, buffer solutions are preferred for liquid formulations, in particular for pharmaceutical liquid formulations. The terms buffer, buffer system and buffer solution, in particular of an aqueous solution, refer to the capacity of the system to resist a pH change by the addition of an acid or a base, or by dilution with a solvent. Preferred buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino) ethanesulfonic acid, maleic acid, cacodylate (dimethyl arsenate), carbonic acid, ADA (N-(2-acetamido)imino diacetic acid, PIPES (4-piperazine-bis-ethanesulfonic acid), BIS-TRIS propane (1,3-bis[tris(hydroxymethyl)mehylaminol] propane), ethylene diamine, ACES (2-[(amino-2-oxoethyl)

amino]ethanesulfonic acid), imidazol, MOPS (3-(N-morphino)-propanesulfonic acid, diethyl malonic acid, TES (2-[tris(hydroxymethyl)methyl]aminoethanesulfonic acid, HEPES (N-2-hydroxyethylpiperazine-N'-2-ethanesulfonic acid), as well as other buffers with a pKa between 3.8 and 7.7.

Preferred are carbonic acid buffers such as acetate buffer and dicarboxylic acid buffers such as fumarate, tartrate and phthalate as well as tricarboxylic acid buffers such as citrate.

A further group of preferred buffers are inorganic buffers such as sulfate hydroxide, borate hydroxide, carbonate hydroxide, oxalate hydroxide, calcium hydroxide and phosphate buffers. Another group of preferred buffers are nitrogen-containing puffers such as imidazol, diethylene diamine and piperazine. Furthermore preferred are sulfonic acid buffers such as TES, HEPES, ACES, PIPES, [(2-hydroxy-1,1-bis-(hydroxymethyl)ethyl)amino]-1-propanesulfonic acid (TAPS), 4-(2-hydroxyethyl)piperazine-1-propanesulfonic acid (EEPS), 4-morpholino-propanesulfonic acid (MOPS) and N,N-bis-(2-hydroxyethyl)-2-aminoethanesulfonic acid (BES). Another group of preferred buffers are glycine, glycyl-glycine, glycyl-glycyl-glycine, N,N-bis-(2-hydroxyethyl)glycine and N-[2-hydroxy-1,1-bis(hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxy proline, N,N,N-trimethyllysine, 3-methyl histidine, 5-hydroxy-lysine, o-phosphoserine, gamma-carboxyglutamate, [epsilon]-N-acetyl lysine, [omega]-N-methyl arginine, citrulline, ornithine and their derivatives.

Preservatives for liquid dosage forms or supplements can be used on demand. They may be selected from the group comprising, but not limited to, sorbic acid, potassium sorbate, sodium sorbate, calcium sorbate, methyl paraben, ethyl paraben, methyl ethyl paraben, propyl paraben, benzoic acid, sodium benzoate, potassium benzoate, calcium benzoate, heptyl p-hydroxybenzoate, sodium methyl para-hydroxybenzoate, sodium ethyl para-hydroxybenzoate, sodium propyl para-hydroxybenzoate, benzyl alcohol, benzalkonium chloride, phenylethyl alcohols, cresols, cetylpyridinium chloride, chlorobutanol, thiomersal (sodium 2-(ethylmercurithio) benzoic acid), sulfur dioxide, sodium sulphite, sodium bisulphite, sodium metabisulphite, potassium metabisulphite, potassium sulphite, calcium sulphite, calcium hydrogen sulphite, potassium hydrogen sulphite, biphenyl, orthophenyl phenol, sodium orthophenyl phenol, thiabendazole, nisin, natamycin, formic acid, sodium formate, calcium formate, hexamine, formaldehyde, dimethyl dicarbonate, potassium nitrite, sodium nitrite, sodium nitrate, potassium nitrate, acetic acid, potassium acetate, sodium acetate, sodium diacetate, calcium acetate, ammonium acetate, dehydroacetic acid, sodium dehydroacetate, lactic acid, propionic acid, sodium propionate, calcium propionate, potassium propionate, boric acid, sodium tetraborate, carbon dioxide, malic acid, fumaric acid, lysozyme, copper-(II)-sulfate, chlorine, chlorine dioxide and other suitable substances or compositions known to the person skilled in the art.

Additional emulsifiers can be selected for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters, polyoxyethene sorbitan monolaurate, polyoxyethene sorbitan monooleate, polyoxyethene sorbitan monopalmitate, polyoxyethene sorbitan monostearate, polyoxyethene sorbitan tristearate, polyoxyethene stearate, polyvinyl alcohol, metatartaric acid, calcium tartrate, alginic acid, sodium alginate, potassium alginate, ammonium alginate, calcium alginate, propane-1,2-diol alginate, carrageenan, processed eucheuma seaweed, locust bean gum, tragacanth, acacia gum, karaya gum, gellan gum, gum ghatti, glucomannane, pectin, amidated pectin, ammonium phosphatides, brominated vegetable oil, sucrose acetate isobutyrate, glycerol esters of wood rosins, disodium phosphate, trisodium diphosphate, tetrasodium diphosphate, dicalcium diphosphate, calcium dihydrogen diphosphate, sodium triphosphate, pentapotassium triphosphate, sodium polyphosphates, sodium calcium polyphosphate, calcium polyphosphates, ammonium polyphosphate, beta-cyclodextrin, powdered cellulose, methyl cellulose, ethyl cellulose, hydroxypropyl cellulose, hydroxypropyl methylcellulose, ethyl methyl cellulose, carboxymethyl cellulose, sodium carboxymethyl cellulose, ethyl hydroxyethyl cellulose, croscarmellose, enzymically hydrolyzed carboxymethyl cellulose, mono- and diglycerides of fatty acids, glyceryl monostearate, glyceryl distearate, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyl tartaric acid esters of mono- and diglycerides of fatty acids, mixed acetic and tartaric acid esters of mono- and diglycerides of fatty acids, succinylated monoglycerides, sucrose esters of fatty acids, sucroglycerides, polyglycerol esters of fatty acids, polyglycerol polyricinoleate, propane-1,2-diol esters of fatty acids, propylene glycol esters of fatty acids, lactylated fatty acid esters of glycerol and propane-1, thermally oxidized soy bean oil interacted with mono- and diglycerides of fatty acids, dioctyl sodium sulphosuccinate, sodium stearoyl-2-lactylate, calcium stearoyl-2-lactylate, stearyl tartrate, stearyl citrate, sodium stearoyl fumarate, calcium stearoyl fumarate, stearyl tartrate, stearyl citrate, sodium stearoyl fumarate, calcium stearoyl fumarate, sodium laurylsulfate, ethoxylated mono- and diglycerides, methyl glucoside-coconut oil ester, sorbitan monostearate, sorbitan tristrearate, sorbitan monolaurate, sorbitan monooleate, sorbitan monopalmitate, sorbitan trioleate, calcium sodium polyphosphate, calcium polyphosphate, ammonium polyphosphate, cholic acid, choline salts, distarch glycerol, starch sodium octenyl succinate, acetylated oxidized starch.

Preferred are glycerin monooleate and stearic acid.

Stabilizers are substances that can be added to prevent unwanted changes. Though stabilizers are not real emulsifiers they may also contribute to the stability of emulsions, respectively solubilisates. Suitable examples for stabilizers are oxystearin, xanthan gum, agar, oat gum, guar gum, tara gum, polyoxyethene stearate, aspartame-acesulfame salt, amylase, proteases, papain, bromelain, ficin, invertase, polydextrose, polyvinyl pyrrolidone, polyvinyl polypyrrolidone, triethyl citrate, maltitol, maltitol syrup.

Suitable as additional surface-active solubilizing agents (solubilizers) are for example diethylene glycol monoethyl ester, polyethyl propylene glycol co-polymers, cyclodextrins such as α- and β-cyclodextrin, glyceryl monostearates such as Solutol HS 15 (Macrogol-15-hydroxystearate from BASF, PEG 660-15 hydroxystearates), sorbitan esters, polyoxyethylene glycol, polyoxyethylene sorbitanic acid esters, polyoxyethylene sorbitan monooleate, polyoxyethylene oxystearic acid triglyceride, polyvinyl alcohol, sodium dodecyl sulfate, (anionic) glyceryl monooleates etc.

Suitable additional solvents may be selected from the group comprising, but not limited to, water, carbonated water, water for injection, water with isotonizing agents, saline, isotonic saline, alcohols, particularly ethyl and n-butyl alcohol, glycols, oleic and linoleic acid triglycerides, caprylic and capric acid mono-, di- and triglycerides, polyoxyethylene caprylic and capric acid glycerides, propylene glycol fatty acid esters, low alkyl fatty acid esters, soy bean oil, propylene glycol laurate, polyoxyethylene (35) castor oil, polyoxyethylene glyceryl trioleate, ethyl butyrate, ethyl caprylate, ethyl oleate and mixtures thereof.

Suitable isotonizing agents are for example pharmaceutically acceptable salts, in particular sodium chloride and potassium chloride, sugars such as glucose or lactose, sugar alcohols such as mannitol and sorbitol, citrate, phosphate, borate and mixtures thereof.

Suitable thickening agents can be selected from the group comprising, but not limited to, polyvinyl pyrrolidone, methyl cellulose, hydroxypropyl methyl cellulose, hydroxypropyl cellulose, dextrins, polydextrose, modified starch, alkaline modified starch, bleached starch, oxidized starch, enzyme-treated starch, monostarch phosphate, distarch phosphate esterified with sodium trimetaphosphate or phosphorus oxychloride, phosphate distarch phosphate, acetylated distarch phosphate, starch acetate esterified with acetic anhydride, starch acetate esterified with vinyl acetate, acetylated distarch adipate, acetylated distarch glycerol, distarch glycerin, hydroxypropyl starch, hydroxy propyl distarch glycerin, hydroxypropyl distarch phosphate, hydroxypropyl distarch glycerol, starch sodium octenyl succinate, acetylated oxidized starch, hydroxyethyl cellulose.

Diluents or fillers are inactive substances added to drugs in order to handle minimal amounts of active agents. They can be useful in the solubilizing process. Examples for suitable diluents are water, mannitol, pre-gelatinized starch, starch, microcrystalline cellulose, powdered cellulose, silicified microcrystalline cellulose, dibasic calcium phosphate dihydrate, calcium phosphate, calcium carbonate, hydroxypropyl cellulose, hydroxyethyl cellulose, hydroxypropyl methylcellulose, polyethylene glycol, xanthum gum, gum arabic or any combination thereof.

Permeation enhancers are often used in topical dosage forms. Suitable permeation enhancers comprise all pharmaceutically acceptable permeation enhancers known in the art, such as, without being limiting, azones such as laurocapran, 1-dodecylazacycloheptan-2-one; sulphoxides such as dimethylsulphoxide, DMAC, DMF; pyrrolidones such as 2-pyrrolidone, N-methyl-2-pyrrolidone; alcohols such as ethanol, 1,2-propandiol or decanol; glycols such as propylene glycol, diethylene glycol, tetraethylene glycol; fatty acids such as oleic acid, lauric acid, sodium lauryl sulfate, myristic acid, isopropyl myristic acid, capric acid; nonic surfactants such as polyoxyethylene-2-oleyl ether, polyoxyethylene-2-stearyl ether; terpenes; terpenoids; oxazolidinones; urea; ceramide analogs, azone analogs, menthol derivatives, etherified derivatives, esterified derivatives, transkarbams, carbamate salts, TXA derivatives, DDAIP (dodecyl 2-(dimethylamino) propanoate), DDAK, natural essential oils (all of them listed in Chen et al. (2014) Asian J. Pharm. Sc. 9, 51-64); citric acid esters such as triethyl citrate; hydrophobin polypeptides; alpha-bisabolol; dimethyl isosorbide (Arlasolve® DMI); ethoxydiglycol. Preferred is 1,2-propandiol.

Typical examples for preservatives suitable for topical applications are e.g. benzyl benzoate, benzoic acid, benzyl alcohol, benzalkonium chloride, N-cetyl-N—N-trimethyl-ammonium bromide (Cetrimid, Merck), chlorhexidine, chlorbutanol, chlorcresol, imidurea, parabens such as methyl, ethyl, propyl or butyl paraben, sodium methylparaben, sodium propylparaben, potassium sorbate, sodium benzoate, sodium propionate, phenol, phenoxyethanol, phenylethyl alcohol, phenylmercuriacetate, phenylmercuriborate, phenylmercurinitrate, sorbic acid or thiomersal (sodium methylmercurithiosalicylate). Preferred are methylparaben, propylparaben as well as sodium methylparaben and sodium propylparaben.

The addition of a sufficient amount of antioxidants is particularly preferable in topical dosage forms. Suitable examples for antioxidants include sodium metabisulfite, alpha-tocopherol, ascorbic acid, maleic acid, sodium ascorbate, ascorbyl palmitate, butylated hydroxyanisol, butylated hydroxytoluene, fumaric acid or propyl gallate. Preferred is the use of sodium metabisulfite.

Suitable pH-regulators for topical dosage forms are e.g. sodium hydroxide, hydrochloric acid, buffer substances such as sodium dihydrogen phosphate or disodium hydrogenphosphate.

Cream preparations may also contain other excipients and additives, such as fatiquors, solvents, consistency enhancers or hydrotopes for improving the flow characteristics. Herein single as well as several substances from the same group of additives or excipients may be present in the mixture.

Suitable fatiquors are e.g. oleic acid decylester, hydrated castor oil, light mineral oil, mineral oil, polyethylene glycol, sodium laurylsulfate.

Suitable solvents are corn oil, cottonseed oil, peanut oil, sesame oil, soybean oil, ethyl oleate, glycerin, isopropyl myristate, isopropyl palmitate, polyethylene glycol or polypropylene glycol.

Consistency enhancers are e.g. cetyl alcohol, cetyl ester wax, hydrated castor oil, microcrstalline waxes, non-ionic emulsifier waxes, beeswax, paraffin or stearylic alcohol.

Suitable hydrotopes are alcohols such as ethanol, isopropyl alcohol or polyols such as glycerin.

According to the invention all of the aforementioned excipients and classes of excipients can be used without limitation alone or in any conceivable combination thereof, as long as the inventive use of a solubilisate is not thwarted, toxic actions may occur or the respective national legislations are infracted.

Thus the present application refers also to a pharmaceutical composition according to the invention for use in medicine.

The present application refers also to a pharmaceutical composition according to the invention for an oral, parenteral or topical administration.

Conditions with a overshooting immune reaction are for example, without being limiting, graft rejection after transplantation, active autoimmune disorders, respectively diseases with an autoimmune component, in particular active rheumatoid arthritis, relapsing-remitting multiple sclerosis, lupoid hepatitis, polyarteritis nodosa, Crohn's disease, colitis ulcerosa, Behçet's disease, Behçet uveitis, idiopathic thrombocytopenic purpura, myasthenia gravis, Lambert-Eaton syndrome, polymyositis, psoriasis, psoriasis arthritis, ankylosing spondylitis, paroxysmal nocturnal hemoglobinuria, autoimmune thyroiditis disorders such as Hashimoto's thyroiditis, Ord's thyroiditis or Graves' disease, Lupus erythematosus, vitiligo, autoimmune encephalomyelitis, idiopathic optic neuritis, sympathetic ophthalmia, anterior uveitis, retina degeneration, peripheral ulcerative keratitis, bullous pemphigoid, chronic urticaria, dermatitis herpetiformis, acquired epidermolysis bullosa, alopecia areata, autoimmune enteropathy, autoimmune polyendocrine syndrome such as APECED (autoimmune polyendocrinopathy-candidiasis-ectodermal dystrophy), Schmidt's syndrome and XPID (X-inked polyendocrinopathy Immunodeficiency and diarrhea syndrome), chronic gastritis, dermatomyositis, diabetes mellitus type 1, diabetes mellitus type 2, Graves' ophthalmopathy, glomerulonephritis, Goodpasture syndrome, granulomatosis with polyangiitis, Guillain-Barre syndrome, Lichen sclerosus, Lichen ruber mucosae, linear IgA dermatosis, microscopic polyangiitis, myalgic encephalomyelitis, narcolepsy, PANS (Pediatric Acute Onset Neuropsychiatric Syndrome) such as. PANDAS (Pediatric Autoimmune Neuropsychiatric Disorders Associated with Streptococcal infections), Pemphigus foliaceus, Pemphigus seborrhoicus, Pemphigus vulgaris, polychondritis, polymyalgia rheumatica, rheumatic fever, SAPHO syndrome (synovitis, acne, pustulosis, hyperostosis, osteitis), sarcoidosis, Sjögren's syndrome, scleroderma, stiff man syndrome, Henoch-Schonlein purpura, celiac disease, acute disseminated encephalomyelitis, antiphospholipid syndrome, autoimmune cardiomyopathy, autoimmune hemolytic anemia, autoimmune inner ear disease, autoimmune lymphoproliferative syndrome, autoimmune pancreatitis, autoimmune polyendocrine syndrome, autoimmune progesterone dermatitis, Chagas disease, chronic inflammatory demyelinating polyneuropathy, chronic recurrent multifocal osteomyelitis, COPD (chronic obstructive pulmonary disease), Churg Strauss syndrome, cold agglutinin disease, Lipomatosis dolorosa, endometriosis, eosinophilic fasciitis, Hashimoto's encephalopathy, acne inversa, interstitial cystitis, Kawasaki disease, Sharp's syndrome, neuromyotonia, opsoclonus myoclonus syndrome, primary biliary cirrhosis, Raynaud's phenomenon, restless legs syndrome, transverse myelitis and vasculitis, aplastic anemia, pemphigus, pemphigoid, endogenous uveitis; nephrotic syndrome and atopic dermatitis; as well as septic conditions such as those induced by infections with gram-negative or gram-positive bacteria such as MRSA (methicillin-resistant *Staphylococcus aureus*), or mycotic pathogens, and systemic inflammatory response syndrome (SIRS) induced by other—for example immunologic or chemical—factors.

Conditions with an immunodeficient background comprise, without being limiting, frequent flu-like infections; recurrent airways infections; recurrent infections of the efferent urinary tract; fatigue; cachexia; concentration disorders of unknown origin; reconvalescence; chronic viral infections, in particular human immunodeficiency viruses such as HIV-1 and HIV-2, hepatitis B, hepatitis C, encephalitis, Herpes zoster, Herpes simplex, inner ear infections, varicella, measles, cytomegaly, Epstein-Barr, adenoviruses, human papilloma viruses and parvoviruses, such as amdoviruses, bocaviruses, dependoviruses, erythroviruses and parvovirus spec., several oncologic diseases, in particular hairy cell leukemia, myeloid leukemia, multiple myeloma, follicular lymphoma, Kaposi sarcoma, cutaneous T cell lymphoma, nasopharyngeal carcinoma, carcinoid, renal carcinoma, urinary bladder carcinoma, basal cell carcinoma, metastasizing carcinoma and malign melanoma; septic granulomatosis, neutropenia; genital warts; keratoses; autoimmune diseases, in particular non-active stages such as relapsing-remitting multiple sclerosis in between the relapses; radiogenic colitis, diverticulitis; allergies, in particular hay fever, polymorphous light eruption, eczema, neurodermitis; enteritis; colitis; as well as before, during and after chemotherapy and radiation.

In resume, a solubilisate of 5-amino-2,3-dihydro-1,4-phthalazinedione produced by the method of the invention is particularly suitable for the treatment of all inflammatory diseases displaying a substantial increase in the release of pro-inflammatory cytokines, in particular of IL-6 und TNF-alpha. Besides the aforementioned examples, this is also the case during wound healing, e.g. after a surgical intervention, trauma or burn, in independent immune processes such as keratitis sicca, or in acute or chronic inflammations of unknown origin such as tendovaginitis or osteoarthritis.

A solubilisate of 5-amino-2,3-dihydro-1,4-phthalazinedione produced by the method of the invention can also be administered in combination with at least one other known pharmaceutically active agent and/or standard therapy.

Thus the present application refers also to a combination of a solubilisate according to the invention and at least one pharmaceutically active agent.

The present application refers likewise to a combination of a solubilisate according to the invention and at least one pharmaceutically active agent for use in the prophylaxis and/or treatment of conditions with an overshooting immune reaction or conditions with an immunodeficient background.

Pharmaceutically active agents suitable for such a combination can be selected from the group comprising steroidal and nonsteroidal anti-inflammatory agents, immunomodulators, immunostimulatory agents, immunosuppressive agents, anti-infective agents, antibiotics, antiviral agents, antifungal agents, antiprotozoal agents, anthelmintics, analgesics, local anesthetics, anticoagulants, antiplatelet drugs, muscle relaxants, tonic agents and anabolic agents. Such a combination of pharmaceutically active agents can be used for prophylactic and/or therapeutic applications in a person in need thereof.

Suitable examples for steroidal anti-inflammatory agents comprise corticosteroids, glucocorticoids, cortisone, cortisone acetate, hydrocortisone, hydrocortisone acetate, dexamethasone, betamethasone, prednisone, prednisolone, methylprednisolone, deltasone, triamcinolone, tixocortol pivalate, mometasone, amcinonide, budesonide, desonide, fluociconide, fluocinolone, halcinonide, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, flunisolide, fluticasone furoate, fluticasone propionate, triamcinolone acetonide, beclomethasone dipropionate.

Suitable examples for nonsteroidal anti-inflammatory agents (NSAIDs) comprise acetylsalicylic acid, salicylic acid and salicylates, paracetamol (acetaminophen), salsalate, diflunisal, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celexoxib, rofecoxib, valdecoxib, parecoxib, lumiracoxib, etoricoxib, firocoxib, nimesulide, clonixin, licofelone, H-harpagide, flunixin, tiaprofenic acid.

Suitable examples for immunomodulators comprise thalidomide, lenalidomide, pomalidomide and apremilast.

Suitable examples for immunostimulatory agents comprise interferons (alpha-, beta-, gamma-, tau-interferon), interleukins, CSF, PDGF, EGF, IGF, THF, levamisole, dimepranol, inosine.

Suitable examples for immunosuppressive agents comprise the group of glucocorticoids such as described above; cytostatics such as alkylating agents (for example cyclophosphamide), antimetabolites such as methotrexate, azathioprine, mercaptopurine, fluorouracil, leflunomide, protein synthesis inhibitors and specific antibiotics such as dactinomycin, anthracyclines, mitomycin C, bleomycin and mithramycin, intercalating agents such as mitoxantrone; antibodies such as muromonab-CD3, rituximab, ustekinumab, alemtuzumab, natalizumab, basiliximab and daclizumab; agents acting on immunophilins such as ciclosporin, tacrolimus and sirolimus; and non-classified immunosuppressive agents such as beta-interferon, gamma-interferon, opioids, TNF-binding proteins such as infliximab, etanercept, adalimumab; or curcumin, catechins, mycophenolic acid, fingolimod, myriocin and fumaric acid dimethyl ester.

Anti-infective agents is a generic term for compounds that can be used in the treatment of bacterial, viral, fungal, protozoal and worm infections and comprise antibiotics, antiviral agents, antimycotics, antiprotozoal agents, anthelmintics and further antiparasitic drugs.

Suitable examples for antibiotics comprise imipenem, meropenem, ertapenem, cephalosporins, aztreonam, penicillins such as penicillin G and penicillin V, piperacillin, mezlocillin, ampicillin, amoxicillin, flucloxacillin, methicillin, oxacillin, clavulanic acid, sulbactam, tazobactam, sultamicillin, fosfomycin, teicoplanin, vancomycin, bacitracin, colistin, gramicidin, polymyxin B, tyrothricin, teixobactin, fosmidomycin, amikacin, gentamicin, kanamycin, neomycin, netilmicin, streptomycin, tobramycin, chloramphenicol, fusidic acid, cethromycin, narbomycin, telithromycin, clindamycin, lincomycin, daptomycin, dalfopristin, quinupristin, azithromycin, clarithromycin, erythromycin, roxithromycin, linezolid, doxycyclin, minocyclin, tetracyclin, oxytetracyclin, tigecyclin, norfloxacin, enoxacin, ciprofloxacin, ofloxacin, levofloxacin, moxifloxacin, metronidazol, tinidazol, aminocoumarin, sulfadiazine, sulfadoxine, sulfamethoxazole, sulfasalazine, pyrimethamine, trimethoprim, rifampicin.

Suitable examples for antiviral agents comprise ancriviroc, aplaviroc, cenicriviroc, enfuvirtid, maraviroc, vicriviroc, amantadine, rimantadine, pleconaril, idoxuridine, aciclovir, brivudine, famciclovir, penciclovir, sorivudine, valaciclovir, cidofovir, ganciclovir, valganciclovir, sofosbusvir, foscarnet, ribavirine, taribavirine, filibuvir, nesbuvir, tegobuvir, fosdevirine, favipiravir, merimepodib, asunaprevir, balapiravir, boceprevir, ciluprevir, danoprevir, daclatasvir, narlaprevir, telaprevir, simeprevir, vaniprevir, rupintrivir, fomivirsen, amenamevir, alisporivir, bevirimat, letermovir, laninamivir, oseltamivir, peramivir, zanamivir.

Suitable examples for antifungal agents comprise abafungin, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, amorolfine, butenafine, naftifine, terbinafine, anidulafungin, caspofungin, micafungin, benzoic acid, ciclopirox, flucytosine, griseofulvin, haloprogin, tolnaftate, undecylic acid, crystal violet, balsam of Peru.

Suitable examples for antiprotozoal agents comprise metronidazole, tinidazole, ornidazole, atovaquone, clioquinol, chlorquinaldol, emetine, pentamidine isethionate, eflornithine, nitrofural, halofuginone, miltefosine, chloroquine, hydroxychloroquine, mepacrine, primaquine, amodiaquine, pamaquine, piperaquine, proguanil, cycloguanil embonate, quinine, mefloquine, pyrimethamine, artemether, artemisinin, artesunate, dihydroartemisinin, halofantrine, lumefantrine, sulfadoxine.

Suitable examples for anthelmintics comprise mebendazole, praziquantel, albendazole, diethylcarbamazine, flubendazole, ivermectin, levamisole, metrifonate, niclosamide, oxyclozanide, oxamniquine, oxantel, piperazine, pyrantel, pyrantel pamoate, monopantel, derquantel, pelletierin sulfate, pyrvinium, thiabendazole, fenbendazole, triclabendazole, abamectin, suramine, emodepside, pyrvinium embonate, aminoacetonitril.

Suitable examples for further antiparasitic drugs comprise meglumine antimoniate, benznidazole, sodium stibogluconate, fumagillin, halofantrine, melarsoprol, nifurtimox, nitazoxanide, permethrin, lindane, malathion, carbaryl, pyrethrum, phenothrin, bio-allethrin, imidacloprid, moxidectin, nitenpyram, fipronil, pyriprol, selamectin, dimpylate, spinosad, indoxacarb, methoprene, pyriproxyfen, lufenuron, neem oil, citronella oil, clove oil, peppermint oil, eucalyptus oil.

Suitable examples for analgesics comprise the NSAIDs listed above; opioid analgesics such as morphine, fentanyl, methadone, oxycodone, carfentanyl, dihydroetorphine, ohmefentanyl, etorphine, sufentanil, remifentanil, alfentanil, buprenorphine, hydromorphone, levomethadone, hydrocodone, pintramide, nalbuphine, tapentadol, pentazocine, dihydrocodeine, codeine, pethidine, tramadol, tilidine, meptazinol, naloxone, naltrexone, diprenorphine, loperamide, apomorphine; epibatidine; scopolamine; ziconitide; cannabinoids such as tetrahydrocannabinol, cannabidiol, marinol; flupirtine; ketamine and the local anesthetics listed above.

Suitable examples for local anesthetics comprise lidocaine, lignocaine, menthol, articaine, bupivacaine, ropivacaine, benzocaine, chloroprocaine, cocaine, cyclomethycaine, dimethocaine, larocaine, piperocaine, propoxycaine, procaine, novocaine, proparacaine, tetracain, amethocaine, cinchocaine, dibucaine, etidocaine, levobupivacaine, meplavacaine, prilocaine, trimecaine, saxitoxin, neosaxitoxin, tetrodotoxin, eugenol.

Suitable examples for anticoagulants comprise heparins, coumarins such as phenprocoumon (Marcumar) and warfarin, apixaban, rivaroxaban, edoxaban, dabigatran, ximelagatran, hirudin, lepirudin, bivalirudin, citrate, EDTA, fondaparinux, argatroban, otamixaban.

Suitable examples for antiplatelet drugs comprise abciximab, acetylsalicylic acid, dipyridamole, clopidogrel, eptifibatide, ilomedine, prostacyclin, prasugrel, ticagrelor, ticlopidine, tirofiban.

Suitable examples for muscle relaxants comprise tercuronium, 1-ethylcarbamoyl-3-(3-trifluoromethylphenyl)pyrrolidine, metaxalone, methocarbamol, meprobamate, baclofen, carisoprodol, chlorzoxazone, cyclobenzaprine, dantrolene, diazepam, orphenadrine, quinine, rocuronium, succinylcholine, decamethonium, pancuronium, veruronium, rapacuronium, dacuronium, duador, malouetine, dipyrandium, pipercuronium, chandonium, HS-342, atracurium, mivacurium, doxacurium, d-tubocurarine, dimethyl tubocurarine, gallamine, alcuronium, anatruxonium, diadonium, fazadinium, tropeinium, cisatrucurium.

Tonic agents is a generic term for agents that strengthen the body, increase the tonus or reestablish its physiological functions. They can be of herbal or animal origin.

Anabolic agents can promote the anabolic metabolism and a strengthening of the cellular collagen scaffold. A far-reaching abuse, however, is known as doping in sports and bodybuilding. Therefore a combination with a solubilisate according to the invention is only recommended inasmuch as a use is covered by the respective national legislations.

A person skilled in the art will easily identify standard therapies for the aforementioned pharmaceutically active agents from the state-of-the-art. It is preferred that the respective modes of administration and dosages of the aforementioned combinations of pharmaceutically active agents orientate themselves on already established standard therapies for the combined active agent.

EXAMPLES

In the ensuing examples the relative quantities of the solubilizing agents can be changed inside the margins indicated for each component in the method according to the invention.

The addition of glyceryl oleate and/or of an antioxidant is optional.

It is possible to upscale or downscale the indicated amounts according to the desired absolute amount of the agent to be solubilized in the solubilisate. The solubilisate can be portioned according to the desired final amount of the agent that shall be administered to a patient in need thereof.

In general, the produced solubilisates produced according to the method of the invention had a specific density of 0.92-0.94 kN/m$^3$.

In each example the production of a dosage form for the solubilisates according to the invention is described for illustrative purposes. It is understood that the solubilisates according to the invention can be also used in any corresponding dosage form known in the art, e.g. as laid out in Remington: The Science and Practice of Pharmacy, 22$^{nd}$ edition, Pharmaceutical Press, 2013, which shall be incorporated by reference.

Standard chemicals were purchased from Sigma-Aldrich, Darmstadt, Germany.

Example 1: Solubilization of 5-amino-2,3-dihydro-1,4-phthalazinedione—Embodiment 1

The following indications refer to the weight percent of the mixture. A solubilisate of ca. 100 ml is generated. 5-amino-2,3-dihydro-1,4-phthalazinedione is provided, and then the solubilizing agents are admixed one by one under stirring for 5 min at room temperature (20±5° C.) and atmospheric pressure.

| | |
|---|---|
| 5-amino-2,3-dihydro-1,4-phthalazinedione | 2.0% |
| non-hydrogenated soybean PC | 46.0% |
| MCT oil | 45.6% |
| mixture of 1-lysophosphatidylcholine and 2-lysophosphatidylcholine (1:1) | 2.2% |
| ethanol | 1.9% |
| oleic acid | 0.8% |
| glyceryl stearate | 1.2% |
| glyceryl oleate | 0.2% |
| alpha-tocopherol | 0.1% |

Then the composition is cautiously heated under continued stirring, with an approximate temperature increment of 1° C./min. After ca. 20 min (ca. 40° C.) the composition starts to become a clear solution. This solubilization process lasts for ca. 16 min more. Thus a solubilisate according to the invention is obtained after ca. 36 min at ca. 56° C. Then the heating and the stirring is stopped and the resulting solubilisate is allowed to cool down to room temperature. The solubilisate stays clear and stable over an observation period of minimum 6 months.

Example 2: Solubilization of 5-amino-2,3-dihydro-1,4-phthalazinedione—Embodiment 2

The following indications refer to the weight percent of the mixture. A solubilisate of ca. 100 ml is generated. 5-amino-2,3-dihydro-1,4-phthalazinedione is provided, and then the solubilizing agents are admixed one by one under stirring for 5 min at room temperature (20±5° C.) and atmospheric pressure.

| | |
|---|---|
| 5-amino-2,3-dihydro-1,4-phthalazinedione | 0.15% |
| 1,2-dioleyl-SN-glycero-3-phosphocholine (DOPC) | 60% |
| MCT oil | 32.45% |
| 1-lysophosphatidylcholine | 2.6% |
| ethanol | 2.2% |
| oleic acid | 1.1% |
| glyceryl stearate | 1.2% |
| glyceryl oleate | 0.2% |
| beta-tocopherol | 0.1% |

Then the composition is cautiously heated under continued stirring, with an approximate temperature increment of 1.5° C./min. After ca. 23 min (ca. 55° C.) the composition starts to become a clear solution. This solubilization process lasts for ca. 10 min more. Thus a solubilisate according to the invention is obtained after ca. 33 min at ca. 70° C. Then the heating and the stirring is stopped and the resulting solubilisate is allowed to cool down to room temperature. The solubilisate stays clear and stable over an observation period of minimum 6 months.

Example 3: Solubilization of 5-amino-2,3-dihydro-1,4-phthalazinedione sodium salt The following indications refer to the weight percent of the mixture. A solubilisate of ca. 100 ml is generated. 5-amino-2,3-dihydro-1,4-phthalazinedione sodium salt (in form of the polymorph Form I as described in WO 2011/107295 A1) is provided, and then the solubilizing agents are admixed one by one under stirring for 5 min at room temperature (20±5° C.) and atmospheric pressure.

| | |
|---|---|
| 5-amino-2,3-dihydro-1,4-phthalazinedione sodium salt | 1.0% |
| non-hydrogenated soybean PC | 70.0% |
| MCT oil | 21.6% |
| 2-lysophosphatidylcholine | 2.6% |
| ethanol | 2.2% |

|  |  |
|---|---|
| oleic acid | 1.1% |
| glyceryl stearate | 1.2% |
| glyceryl oleate | 0.2% |
| delta-tocopherol | 0.1% |

Then the composition is cautiously heated under continued stirring, with an approximate temperature increment of 1° C./min. After ca. 32 min ca. (52° C.) the composition starts to become a clear solution. This solubilization process lasts for ca. 8 min more. Thus a solubilisate according to the invention is obtained after ca. 40 min at ca. 60° C. Then the heating and the stirring is stopped and the resulting solubilisate is allowed to cool down to room temperature. The solubilisate stays clear and stable over an observation period of minimum 2 months.

Example 4: Preparation of a Liquid Dosage Form for Oral Application

In 45 ml of a liquid carrier having the following composition (in weight-%)

|  |  |
|---|---|
| water for injection | 99.3% |
| citrate buffer | 0.5% |
| methyl paraben + propyl paraben (ratio 5:1) | 0.1% |
| sodium metabisulfite | 0.1% |

5 ml of the solubilisate of Example 1 are solved. This solution (50 ml) can be filled into a suitable dropper bottle known in the art.

This formulation does not need an additional emulsifier such as a polysorbate.

Example 5: Preparation of a Liquid Dosage Form for Parenteral Application

In 245 ml of a liquid carrier having the following composition (in weight-%)

|  |  |
|---|---|
| water for injection | 98.9% |
| sodium chloride | 0.9% |
| methyl paraben + propyl paraben (ratio 10:1) | 0.1% |
| sodium metabisulfite | 0.1% |

5 ml of the solubilisate of Example 1 are solved. This parenteral solution (250 ml) can be filled into a suitable infusion bag known in the art.

This formulation does not need an additional emulsifier such as a polysorbate.

Example 6: Preparation of a Solid Dosage Form as Soft Gelatin Capsules

Composition of the Soft Gelatin Capsule Shell (in Weight-%):

|  |  |
|---|---|
| gelatin | 66.3% |
| glycerin | 33.0% |
| methyl paraben + propyl paraben (ratio 4:1) | 0.1% |
| carmoisine | 0.1% |
| titanium dioxide | 0.5% |
| aqua dest. | 1.3 × of gelatin |

A soft gelatin capsule containing a solubilisate of 5-amino-2,3-dihydro-1,4-phthalazinedione is produced according to standard methods, as laid out in: Mahato and Narang, Pharmaceutical Dosage Forms and Drug Delivery, 2$^{nd}$ ed., chap. 18.3.5. Herein, 1.25 ml of the solubilisate of Example 1 are injected into the die cavity of the provided soft gelatin capsule which is then sealed.

Example 7: Preparation of a Solid Dosage Form as Hard Gelatin Capsules

Composition of the Hard Gelatin Capsule Shell (in Weight-%):

|  |  |
|---|---|
| gelatin | 85.0% |
| water | 14.3% |
| methyl paraben + propyl paraben (ratio 4:1) | 0.1% |
| sunset yellow | 0.1% |
| titanium dioxide | 0.5% |

Hard gelatin capsules (size "000", having a volume of 1.4 ml) are produced by a standard method known in the art. 1.25 ml of the solubilisate as produced in Example 1 are filled into a capsule, respectively. Thereupon the two pieces of the hard gelatin capsules are assembled.

Example 8: Preparation of a Topical Dosage Form as a Cream

The Following Ingredients are Used (in Weight-%):

|  |  |
|---|---|
| solubilisate of 5-amino-2,3-dihydro-1,4-phthalazinedione, as of Example 1 | 3.00% |
| cetearyl alcohol (Lanette D ®) | 6.60% |
| glyceryl stearate (Cutina MD ®) | 4.15% |
| ceteareth 20 (Eumulgin B2 ®) | 0.40% |
| ceteareth 12 (Eumulgin B1 ®) | 1.25% |
| decyl oleate (Cetiol V ®) | 2.50% |
| allantoin | 0.15% |
| sodium cetearyl sulfate (Lanette E ®) | 0.65% |
| glycerin | 20.70% |
| phenoxyethanol, dehydroacetic acid, benzoic acid (Rokonsal ND ®) | 1.00% |
| aqua | 59.60% |

In a first preparation, the solubilisate of 5-amino-2,3-dihydro-1,4-phthalazinedione, cetearyl alcohol, glyceryl stearate, ceteareth 20, ceteareth 12, decyl oleate and sodium cetearyl sulfate are mixed and heated to 70° C. In a second preparation, allantoin, glycerin and aqua are mixed and heated to 70° C. Then the first preparation and the second preparation are slowly mixed and homogenized with a disperser (Ultra-Turrax T-18®) for 2-3 min. When cooled down to 35° C., a third preparation consisting of Rokonsal ND® is added and homogeneously stirred. The mixture is rehomogenized at ca. 45° C. for 1 min. Then the resulting mixture is allowed to cool down to room temperature under stirring, herein avoiding the inclusion of air. If necessary, the pH can be adjusted with NaOH or citric acid.

The pH of the cream is 5.40. The stability of the skin cream was minimum 6 months at 40° C. At this temperature no phase separation occurred.

50 ml of the resulting cream are packaged into a collapsible suitable aluminum tube known in the art.

Example 9: Preparation of a Topical Dosage Form as a Hydrogel

A hydrogel is generated by slight modifications of the method disclosed in US 2010/0129448 A1.

A 3% CMC (carboxy-methyl-cellulose) solution is made by mixing 5 ml of the solubilisate of Example 1 with WFI (water for injection) followed by autoclaving to dissolve fully the CMC into solution, resulting in the formation of a CMC hydrogel. A suspension is made by adding said solubilisate solved in WFI into the CMC hydrogel. Stabilizers (TEA, citric acid) are added to the CMC hydrogel. The resulting combination is mixed under high shear conditions (paddle mixer and sonication) as described in US 2005/0175707 at elevated temperature (40 to 50° C.). Glycerol and additional WFI are also added to the suspension. The amount of excipients added to the hydrogel is controlled to achieve a desired concentration of containing 5-amino-2,3-dihydro-1,4-phthalazinedione.

The 3% CMC hydrogel suspension is further mixed for 20 minutes, resulting in the formation of a bulk hydrogel suspension. The bulk hydrogel suspension is observed under an optical microscope at 100× magnification. The primary particle size of the suspended particles is less than ca. 10 µm, thus permitting topical application of the composition to open wounds or other tissues without abrasion.

Example 10: Preparation of a Solid Dosage Form as a Suppository

Composition of the Suppository Base (in Weight-%):

| | |
|---|---|
| cocoa butter | 97.9% |
| ascorbic acid | 0.1% |
| aluminum monostearate | 2.0% |

1) For melting, the suppository base is heated to 50-52° C. Then the melted fatty base is slowly cooled down to 36° C.
2) For each suppository to be cast the respective amount of 0.5 ml of the solubilisate of Example 3 is added to the fatty base. A soft base is formed.
3) Said soft base is filled into a suppository mold configured for the production of 3 cm long torpedo-shaped rectal suppositories having a weight of ca. 2 g.
4) The suppositories are let to cool down to room temperature and then are collected.

The use of the solubilisate according to the invention allows for the production of suppositories without the use of an additional emulsifier and/or a plasticizer. Thus such a suppository according to the invention is free of polysorbate.

The invention claimed is:

1. A method for solubilizing an orally administered pharmaceutically active agent, wherein said pharmaceutically active agent is 5-amino-2,3-dihydro-1,4-phthalazinedione, comprising:
   a) providing the orally administered pharmaceutically active agent in the overall range of 0.1% to 25% per weight at room temperature and atmospheric pressure;
   b) adding in any sequence the solubilization agents of at least one phosphatidylcholine in the overall range of 20% to 80% per weight,
   wherein the at least one phosphatidylcholine is non-hydrogenated soybean PC, DMPC, POPC or DOPC,
   at least one medium-chained triglyceride in the overall range of 10% to 70% per weight,
   at least one lysophosphatidylcholine in the overall range of 1% to 15% per weight,
   wherein the ratio of phosphatidylcholines to lysophosphatidylcholines is in the range of 80:1 per weight to 1.33:1 per weight,
   at least one $C_2$ to $C_4$ alcohol in the overall range of 1% to 20% per weight, and
   at least one of glyceryl stearate and or a saturated or unsaturated $C_{14}$ to $C_{20}$ fatty acid in the overall range of 0.5% to 10% per weight, respectively,
   wherein the relative weight percentages of all ingredients add up to 100% and each solubilization agent is a food additive, a pharmaceutically acceptable excipient, or both;
   c) heating the resulting mixture by continuously increasing the temperature with a continuous temperature increment of 0.5° C./min-3° C./min over a period of 20-60 minutes;
   d) stopping the temperature increase in a temperature range of 30° ° C. to 125° C. as soon as a clear solubilisate is achieved; and
   e) letting the resulting solubilisate cool down to room temperature,
   wherein the resulting solubilisate is a clear solution, water-free and suitable for storage and production of a pharmaceutical oral dosage from.

2. The method according to claim 1, wherein 5-amino-2,3-dihydro-1,4-phthalazinedione is provided in form of a sodium, potassium or lithium salt or a mixture thereof in the overall range of 0.1% to 2% per weight at room temperature and atmospheric pressure.

3. The method according to claim 1, wherein said at least one saturated or unsaturated $C_{14}$ to $C_{20}$ fatty acid is oleic acid.

4. The method according to claim 1, wherein said at least one $C_2$ to $C_4$ alcohol is ethanol.

5. The method according to claim 1, wherein additionally in step b) at least one antioxidant in the overall range of 0.01 to 10% per weight is added, said at least one antioxidant being a pharmaceutically acceptable excipient.

6. The method according to claim 5, wherein said at least one antioxidant is ascorbyl palmitate and/or at least one tocopherol.

7. The method according to claim 4, wherein additionally in step b) ascorbyl palmitate in the overall range of 0.01 to 10% per weight is added.

8. The method according to claim 2, wherein said at least one saturated or unsaturated $C_{14}$ to $C_{20}$ fatty acid is oleic acid.

* * * * *